United States Patent
El-Sebaie et al.

(10) Patent No.: US 12,214,105 B2
(45) Date of Patent: Feb. 4, 2025

(54) LONG LASTING BIODEGRADABLE POLYMER BASED IN-SITU FORMING IMPLANT FOR TREATMENT OF BONE INJURIES

(71) Applicant: FUTURE UNIVERSITY IN EGYPT, New Cairo (EG)

(72) Inventors: Fatma Samir Abd El-Salam El-Sebaie, Giza (EG); Seham Abd Elkhalek Elkheshen, Cairo (EG); Azza Ahmed Mohamed Mahmoud, Cairo (EG); Nermeen Adel Ahmed Elkasabgy, Giza (EG); Emad Basalious Bashir Basalious, Cairo (EG); Amany Abdel Monem Mostafa Abdel Rahman, Giza (EG); Mohammed Said Mostafa Amer, Giza (EG)

(73) Assignee: FUTURE UNIVERSITY IN EGYPT, New Cairo (EG)

( * ) Notice: Subject to any disclaimer, the term of this patent is extended or adjusted under 35 U.S.C. 154(b) by 664 days.

(21) Appl. No.: 17/436,862

(22) PCT Filed: Mar. 5, 2019

(86) PCT No.: PCT/EG2019/050002
§ 371 (c)(1),
(2) Date: Sep. 7, 2021

(87) PCT Pub. No.: WO2020/177830
PCT Pub. Date: Sep. 10, 2020

(65) Prior Publication Data
US 2022/0152270 A1    May 19, 2022

(51) Int. Cl.
A61L 27/18    (2006.01)
A61K 31/4535    (2006.01)
(Continued)

(52) U.S. Cl.
CPC .......... *A61L 27/18* (2013.01); *A61K 31/4535* (2013.01); *A61L 27/54* (2013.01);
(Continued)

(58) Field of Classification Search
CPC .......... A61L 27/18; A61L 27/54; A61L 27/58; A61L 2400/06; A61L 2430/02;
(Continued)

(56) References Cited

U.S. PATENT DOCUMENTS 4,938,763 A    7/1990 Dunn et al.
5,599,552 A    2/1997 Dunn et al.
(Continued)

OTHER PUBLICATIONS

International Search Report for PCT/EG2019/05002 issued Jun. 12, 2019.
(Continued)

*Primary Examiner* — Trevor Love
*Assistant Examiner* — Janet Joseph
(74) *Attorney, Agent, or Firm* — Schmeiser, Olsen & Watts, LLP

(57) ABSTRACT

A pharmaceutical composition capable of forming free burst release effect in-situ forming implant useful for injection inside bone injuries without surgery is provided. This pharmaceutical composition includes; biodegradable polymer, selective estrogen receptor modulator, organic solvent and liquid lipid, solidifies upon contacting with the surrounding medium and form solid implant with compact framework by in-situ phase separation method to deliver the selective estrogen receptor modulator. This compact framework restores the porous structure of the implant by time which is essential in promoting bone healing.

10 Claims, 5 Drawing Sheets

(51) Int. Cl.
*A61L 27/54* (2006.01)
*A61L 27/58* (2006.01)

(52) U.S. Cl.
CPC ............ *A61L 27/58* (2013.01); *A61L 2400/06* (2013.01); *A61L 2430/02* (2013.01)

(58) Field of Classification Search
CPC .......... A61L 2300/412; A61K 31/4535; A61K 9/0024; A61K 47/14; A61K 47/20; A61K 47/34; A61K 2300/00; A61P 19/00; C08L 67/04
See application file for complete search history.

(56) References Cited

U.S. PATENT DOCUMENTS

| | | | |
|---|---|---|---|
| 5,744,153 | A | 4/1998 | Yewey et al. |
| 6,630,155 | B1 | 10/2003 | Chandrashekar et al. |
| 2003/0082234 | A1* | 5/2003 | Seo ........................ A61K 47/34 424/85.2 |
| 2005/0048123 | A1 | 3/2005 | Su et al. |
| 2014/0314864 | A1* | 10/2014 | Cheng ................ A61K 47/6937 424/130.1 |

OTHER PUBLICATIONS

Written Opinion for PCT/EG2019/05002 issued Jun. 12, 2019.
Siyu Dong: "An in situ-forming. solid lipid/PLGA hybrid implant for long-acting antipsychotics". The royal society of chemistry • vol. 7 • 2011 • p. 5873-5878 [The Whole Document].

* cited by examiner

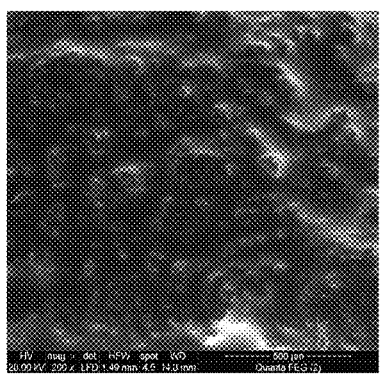 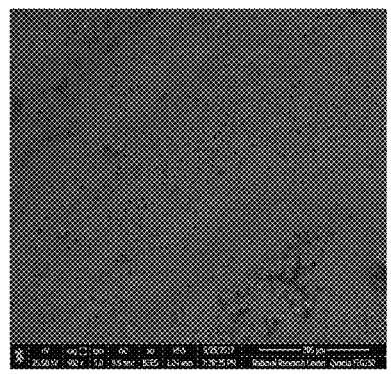 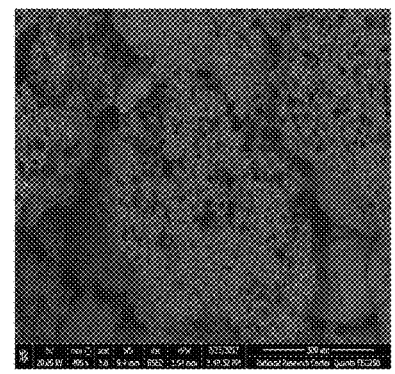
Fig. 7A                      Fig. 7B                      Fig. 7C

| 3 weeks | 6 weeks | 12 weeks |

LONG LASTING BIODEGRADABLE POLYMER BASED IN-SITU FORMING IMPLANT FOR TREATMENT OF BONE INJURIES

CROSS-REFERENCE TO RELATED APPLICATIONS

This application claims priority to PCT Application No. PCT/EG2019/050002, having a filing date of Mar. 5, 2019, the entire contents of which are hereby incorporated by reference.

FIELD OF TECHNOLOGY

The following relates to injectable long lasting biodegradable polymer based in-situ forming implant formulations for treatment of bone injuries.

BACKGROUND

Bone repair especially of large bone defects resulting from severe trauma, resection of bone tumours or reduced normal bone regeneration in case of cancer, vascular necrosis and osteoporosis, remains a great challenge in the field of orthopaedic surgery. Surgical treatment is the first line treatment in some cases but sometimes the post-surgical healing may be delayed due to other health issues or age. There are currently a number of treatment methods available in the surgical field which can be used for enhancement or management of these complex clinical situations for example; tissue engineering, the use of natural bone grafts or metallic prosthetic implants. Although all these methods may be used successfully in certain orthopedic applications they suffer from some disadvantages like post operative pain and complications, blood loss or hematomas, infection, fracture, neurovascular injury, as well as cosmetic deformity and long operative time.

Various options have been explored to produce injectable sustained release of oseteoinductive and osteoconductive drugs with reduced side effects. Injectable drug delivery systems possess many advantages, which include the ease of application, localized delivery for a site-specific action, prolonged delivery periods and improved patient compliance. Initial studies examined delivery systems such as: emulsions, liposomes, microspheres and micelles. But unfortunately, these systems suffer from some stability problems, low drug entrapment and sterilization problems.

Alternative approaches have been made to develop compositions which can be injected easily inside bone injuries using natural and synthetic biodegradable polymers namely in-situ forming implants (ISFI). They are classified according to their origin into natural and synthetic polymers. Natural polymers such as: gellan gum, alginic acid, chitosan, pectin and xyloglucan and synthetic biodegradable polymers like: aliphatic polyesters such as poly (lactic acid), poly (glycolic acid), poly (lactide-co-glycolide) (PLGA), poly (decalatone) and poly-ε-caprolactone. Various other synthetic polymers like triblock co-polymer composed of poly (D,L-lactide)-block-poly(ethylene glycol)-block-poly(DL-lactide), blends of low molecular weight poly(D,L-lactide) and poly(ε-caprolactone) were used also as biodegradable polymers in ISFI.

ISFI systems were previously described in the U.S. Pat. Nos. 4,938,763 and 5,599,552. Once these systems are injected in the body fluid they solidify to form a semisolid depot which is characterised by sustained release of the drug over an extended period of time without the need of multiple injections or oral doses. In-situ solidification or gelling can be triggered by several conditions; changes in pH, temperature, water concentration and changes in specific ion concentrations. Accordingly, In-situ forming biodegradable implants can be classified into four categories: thermoplastic pastes, in-situ cross linked systems, in-situ phase separation systems and in-situ solidifying organogels.

PLGA ISFI are generally prepared by the in-situ phase separation method in which the PLGA is dissolved in a water miscible, non-toxic and biocompatible solvent such as; N-methyl-2-pyrrolidone, dimethyl sulfoxide (DMSO), triacetin, benzyl benzoate and ethyl acetate, which diffuses out of the polymer upon contact with the aqueous medium and then water diffuses into the polymer matrix resulting in polymer precipitation and hence, a solid polymeric implant is formed.

One of the most important advantages of ISFI in the treatment of bone injuries is the ease of injection in the site of action. Once the ISFI formulation is injected in the aqueous medium, the water miscible solvent diffuses to the aqueous environment resulting in the formation of interconnected pores in the solidified polymeric matrix. This porous structure allows the diffusion of cell nutrients and the invasion of tissues and blood capillaries.

In spite of the importance of this porous structure for bone regeneration; it is considered the main cause of the initial burst drug release that the PLGA ISFIs suffer from. This initial burst effect results in difficulty in maintaining constant plasma drug concentration throughout the treatment regimen and it may increase the incidence of drug toxicity especially in drugs which have narrow therapeutic index.

Therefore, there were several attempts to reduce the initial burst effect in PLGA in-situ forming implants. Examples of polymeric in-situ forming implants were described in U.S. Pat. No. 6,630,155, the composition described in this patent comprising PLGA, poly(lactide-co-glycolide)/poly-ethylene glycol block co-polymer, organic solvent and a biologically active agent. PLGA/PEG block co-polymer was used in these compositions to reduce the initial burst release effect. But this composition had two problems; first, PLGA/PEG block co-polymer cannot be used as a base polymer to reduce the burst release, it must be combined with another base polymer. Second, the molecular weight of PLGA/PEG block co-polymer should be relatively high with intrinsic viscosity more than 0.8 dl/g to reduce the initial burst release of the biologically active agent. This high molecular weight with increased intrinsic viscosity will result in difficulty in the injectability of the formulations.

U.S. Pat. No. 5,744,153 discloses incorporation of drug into microstructures, such as liposheres, liposomes, microcapsules, microparticles, and nanoparticles followed by suspending this microstructure into liquid implant. However, the method of preparing these formulations is time consuming as it requires first preparing the microstructures containing the drug, then preparing the liquid implant. Moreover, these microsystems usually have the disadvantage of low drug entrapment.

Some patent applications suggested the use of polyethylene glycol as a polymeric solvent for the used biodegradable polymers in the in-situ forming implant formulations for example: U.S. patent application No. 2005/0048123 provides a liquid controlled release drug delivery compositions which gel upon injecting into the body, to form in-situ controlled release drug implant. The application provided an in-situ gelling formulations comprising a drug substance, and a PLGA polymer dissolved or dispersed in polyethylene glycol (PEG) as a liquid phase solvent. However, the U.S. patent application 2003/0082234, stated that PEG is not a suitable solvent for PLGA, and it requires mixing at high temperatures of 80° C. to obtain uniform composition. Moreover, this composition undergoes phase separation when it stands for a long period of time due to the lower affinity of polylactide, polglycolide and their copolymers with PEG.

U.S. patent application provided a liquid composition of drug delivery implant which comprises; biodegradable polymer, a water soluble biocompatible polyethylene glycol derivative and a pharmacologically active substance. The biodegradable polymer, a water soluble biocompatible polyethylene glycol derivative and a pharmacologically active substance are dissolved in an organic solvent then the organic solvent removed by lyophilisation.

Dong et al in Soft Matter, Vol. 7, 2011, entitled "An in situ-forming, solid lipid/PLGA hybrid implant for long-acting antipsychotics", reduced the burst release of risperidone from PLGA-ISFI by incorporating solid lipids like stearic acid and glyceryl monostearate in the polymeric matrix. Solid lipids formed a compact framework, which is responsible for the reduced initial burst release. This compact framework lacks the porous structure, required for bone regeneration.

Consequently, there is a need for sustained release injectable burst free PLGA-based in-situ forming implant formulations. Such formulations allow the restoration of the porous structure of the formed implant which is essential in the healing of bone injuries.

SUMMARY

An aspect relates to burst free pharmaceutical compositions capable of forming in-situ implants useful for injection inside bone injuries without surgery which solidify upon contacting with the surrounding medium and form solid or semi-solid implant with compact framework by in-situ phase separation method to deliver biologically active drug for prolonged period of time. This compact framework restores the porous structure of the implant by time which is essential in promoting bone healing.

In an embodiment of the present invention the pharmaceutical composition capable of forming burst free in-situ forming implant comprises selective estrogen receptor modulator (SERM), biodegradable polymer which is poly-(lactide-co-glycolide) copolymer, liquid lipid and a biocompatible organic solvent that is miscible with water.

In another embodiment of this invention a method for preparation of in-situ forming implant pharmaceutical compositions comprises the following steps:
  a) Dissolving a biodegradable polymer in an organic solvent miscible with water;
  b) Sonicating the polymer solution for 15 minutes;
  c) Refrigerating the polymer solution at 4° C. overnight;
  d) Dissolving an accurately weighed amount of a selective estrogen receptor modulator in a liquid lipid;
  e) Mixing the polymer solution with the liquid lipid and the selective estrogen receptor modulator mixture;
  f) Sterilizing the in-situ forming implant formulation by Gamma radiation.

In another embodiment of the present invention a method for treatment of bone injury comprises injecting the in-situ forming implant pharmaceutical compositions inside the injury through the skin without surgery.

BRIEF DESCRIPTION

Some of the embodiments will be described in detail, with references to the following Figures, wherein like designations denote like members, wherein:

FIG. 7A depicts a scanning electron microscopy of surface view of LLL-IFI$_{11}$ 24 h after injection into the buffer medium;

FIG. 7B depicts a scanning electron microscopy of surface view of LLL-IFI$_{11}$ 168 h after injection into the buffer medium;

FIG. 7C depicts scanning electron microscopy of surface view of LLL-IFI$_{11}$ 720 h after injection into the buffer medium;

Figure 8A:
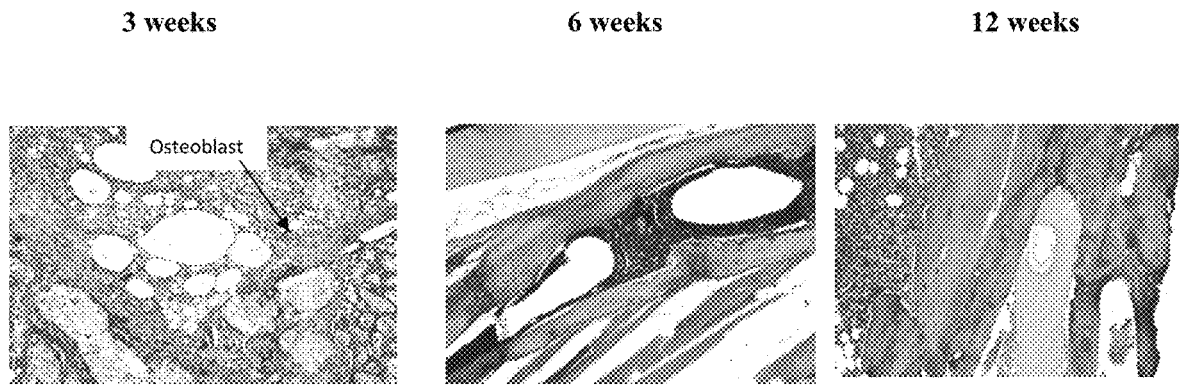
FIG. 8A depicts a histological section of punctures in the tibia of rats stained with hematoxylin and eosin in a non-treated tibial puncture after 3, 6 and 12 weeks of treatment.
Figure 8B:
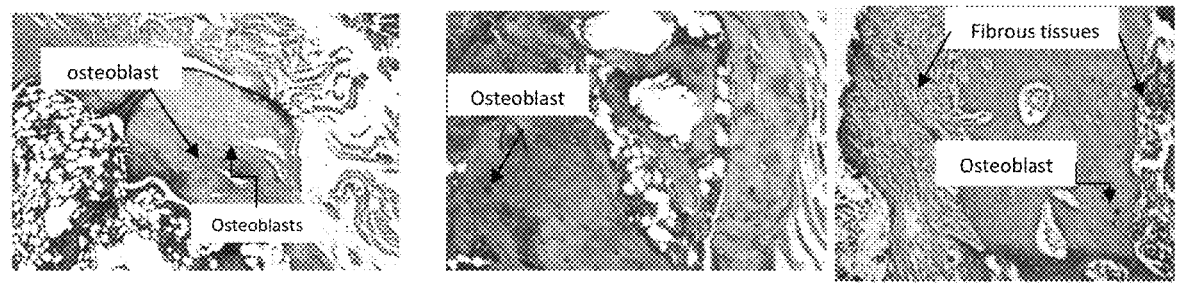
Figure 8C:
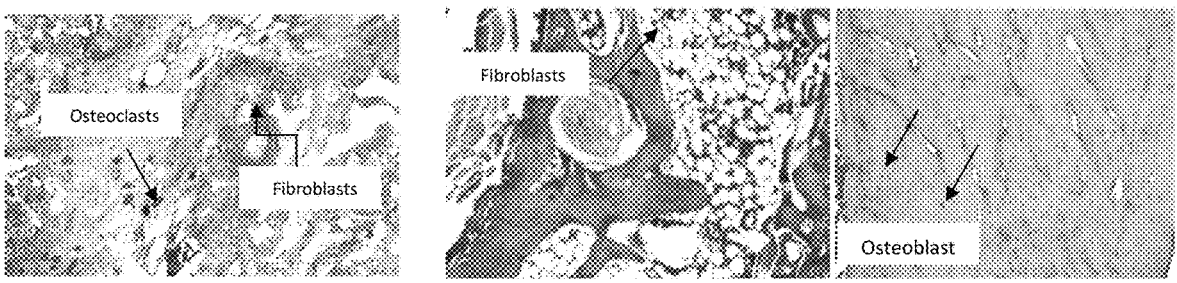

FIG. 8B depicts a histological section of punctures in the tibia of rats stained with hematoxylin and eosin in a tibial puncture treated with P75/25-ET$_1$ after 3, 6 and 12 weeks of treatment; and FIG. 8C depicts a histological section of punctures in the tibia of rats stained with hematoxylin and eosin in a tibial puncture treated with LLL-IFI$_{11}$ after 3, 6 and 12 weeks of treatment.

DETAILED DESCRIPTION

As used herein, "in-situ forming implant (IFI)" is used to indicate that solid or semi-solid implant structure is formed after injecting a pharmaceutical composition inside a mammalian, which release the drug for prolonged period of time.

The phrase "pharmaceutical composition capable of forming in-situ implant" is defined herein as the pharmaceutical composition which forms solid or semi-solid structure upon contacting with body fluid.

In embodiments of the invention the phrase "pharmaceutical composition" is used interchangeably with the word "formulations".

The term "burst release effect" as used herein denotes undesirable increase in the drug release in the first 24 hours after administration of the pharmaceutical composition.

The phrase, "prolonged period of time" is used herein to indicate that the drug released from the formed implant extended from 3 weeks to about 2 months.

The term "biodegradable polymer" is used in embodiments of the invention to indicate the polymer that gradually decomposes, dissolves and/or erodes in-vivo. The biodegradable polymer used here in embodiments of the invention is poly-(lactic-co-glycolic acid) (PLGA) with different ratios of lactide to glycolide moieties; for example, 50:50 PLGA, 65:35 PLGA, 75:25 PLGA and 85:15 PLGA.

In embodiments, the biodegradable polymer can be present in concentrations ranged from 5%-40% w/v, for example, from 7%-30% w/v.

The term "biocompatible organic solvent" herein may included, but is not limited to, N-methyl-2 pyrrolidone, tetrahydrofuran, methyl acetate, ethyl acetate, dimethyl formamide, dimethyl sulfoxide, dimethylsulfone, triacitin and propylene glycol. In embodiments of the present invention the concentration of the biocompatible organic solvent can be taken in the range of 10% to 90% w/v of the composition, for example, 50% to 85% w/v of the composition.

As used herein the term "drug" is used to indicate selective estrogen receptor modulators (SERMs) which are not limited to tamoxifene, tormifene, raloxifene and bazedoxifene, and their pharmaceutically acceptable salts.

The phrase "liquid lipids" in embodiments of the invention is used to indicate caprylocaproyl macrogol-8 glycerides (Labrasol®), caprylic/capric triglyceride (Labrafac®), 1-monoolein and 1-monolinolein which are used in embodiments of the invention in concentrations ranged from 2.5%-30% w/v, for example, from 5%-25% w/v.

Comparative Example 1: Preparation of PLGA in-situ forming implant formulations PLGA homogenous solution was prepared by dissolving PLGA in DMSO in screw-capped glass vials. Then the mixture is kept in refrigerator at 4° C. over night. Accurately weighed amount of SERMs equivalent to a concentration of 10 mg/mL was added to the PLGA solution then vortexed (vortex; JulaboLabortechnik, Germany) for 3 min till complete dissolution of the drug. Table-1 shows the composition of the prepared PLGA-IFI loaded with raloxifene hydrochloride.

TABLE 1

Composition of PLGA in-situ forming implant formulations

| Formulation code | PLGA Type | Concentration (% w/v) |
|---|---|---|
| P50/50-AT$_1$ | Carboxylic acid terminal | 10 |
| P50/50-AT$_2$ | 50:50 lactide:glycolide ratio | 20 |
| P50/50-AT$_3$ | | 30 |
| P50/50-ET$_1$ | Ester terminal | 10 |
| P50/50-ET2 | 50:50 lactide:glycolide ratio | 20 |
| P50/50-ET$_3$ | | 30 |
| P75/25-ET$_1$ | Ester terminal | 10 |
| P75/25-ET$_2$ | 75:25 lactide:glycolide ratio | 20 |
| P75/25-ET$_3$ | | 30 |

Example 2

Formulations are prepared as mentioned in example 1, except that 10% w/v liquid lipid component caprylocaproyl macrogol-8 glycerides (Labrasol®), caprylic/capric triglyceride (Labrafac®), 1-monoolein and 1-monolinolein was dispersed in the DMSO prior to the addition of both PLGA and the drug (table 2).

TABLE 2

Composition of liquid lipid-based PLGA in-situ forming formulations

| Formulation code | PLGA Type | PLGA Concentration (% w/v) | Liquid lipid Type | Liquid lipid Concentration (% w/v) |
|---|---|---|---|---|
| LLL-AT$_1$ | Carboxylic acid terminal 50:50 lactide:glycolide | 10 | Labrasol ® | 10 |
| LLL-AT$_2$ | | 10 | Labrafac ® | 10 |
| LLL-AT$_3$ | | 10 | 1-Monolinolein | 10 |
| LLL-AT$_4$ | | 10 | 1-Monoolein | 10 |
| LLL-ET$_5$ | Ester terminal 50:50 lactide:glycolide | 10 | Labrasol ® | 10 |
| LLL-ET$_6$ | | 10 | Labrafac ® | 10 |
| LLL-ET$_7$ | | 10 | 1-Monolinolein | 10 |
| LLL-ET$_8$ | | 10 | 1-Monoolein | 10 |
| LLL-ET$_9$ | Ester terminal 75:25 lactide:glycolide | 10 | Labrasol ® | 10 |
| LLL-ET$_{10}$ | | 10 | Labrafac ® | 10 |
| LLL-ET$_{11}$ | | 10 | 1-Monolinolein | 10 |
| LLL-ET$_{12}$ | | 10 | 1-Monoolein | 10 |

In-Vitro Drug Release Method

Using the dialysis bag diffusion technique, each dialysis bag was filled with 1.5 mL phosphate buffer saline solution (pH 7.4) for implant formation. Accurately measured volume of 1 mL of the investigated formulation loaded with 10 mg of the drug was injected into the dialysis bag (6 cm long) which was soaked in distilled water for 12 h in advance. Each dialysis bag was secured using two clamps at both ends and placed in a glass bottle pre-filled with 50 mL of the release medium (distilled water and 0.1% w/v Tween® 80). The glass bottles were then incubated in an incubator shaker (Unimax, IKA, Germany) shaken at 90 strokes/min and maintained at 37±0.5° C. The total amount of the release medium (50 mL) was replaced with fresh medium at preset time intervals to preserve the sink conditions.

The amount of raloxifene HCl in the release medium was analyzed spectrophotometrically at 280 nm using UV spectrophotometer (T80 UV-VIS spectrophotometer, PG instruments, Bejing, China).

Figure 1:
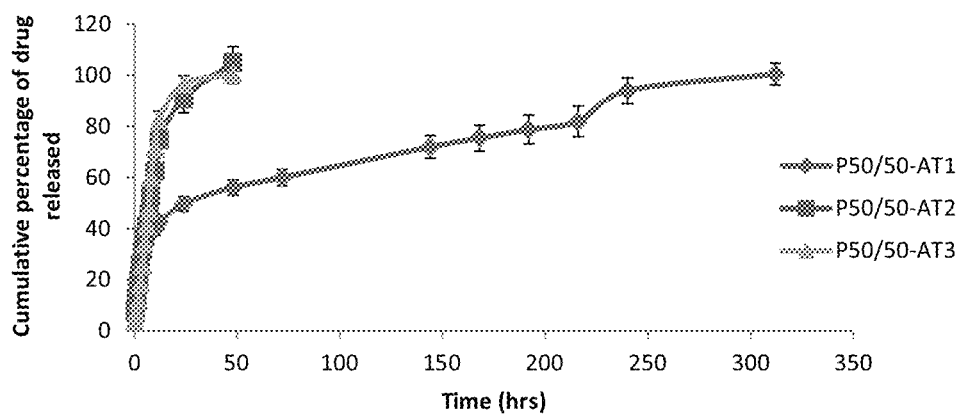
FIG. 1 depicts release profiles of raloxifene hydrochloride from in-situ forming implant formulations prepared from PLGA lactide to glycolide ratio of 50:50 with carboxylic acid-terminal group.
Figure 2:
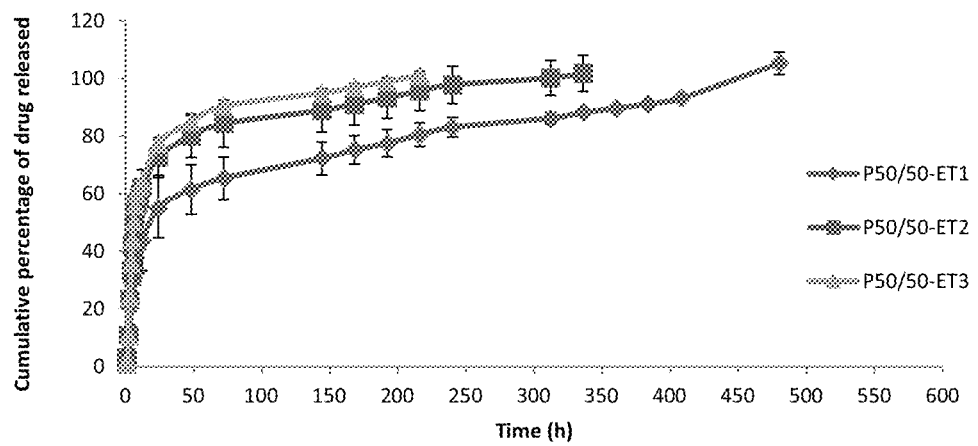
FIG. 2 depicts release profiles of raloxifene hydrochloride from in-situ forming implant formulations prepared from PLGA lactide to glycolide ratio of 50:50 with ester-terminal group.
Figure 3:
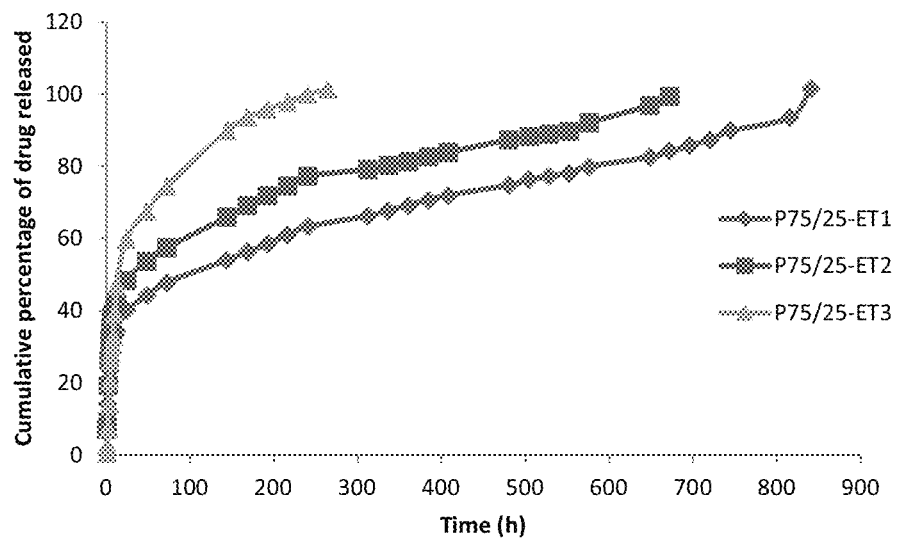
FIG. 3 depicts release profiles of raloxifene hydrochloride from in-situ forming implant formulations prepared from PLGA lactide to glycolide ratio of 75:25 with ester-terminal group.

The in-vitro release of RLX hydrochloride from PLGA-based in-situ implant formulations All the tested formulations in Table 1 suffered from initial burst drug release (ranged from 35% to 96% of drug release within 24 h). This burst effect was due to the formation of porous matrix within the first 24 hours which assists the penetration of the dissolution medium and extraction of the drug (FIGS. 1-3).

Figure 4:
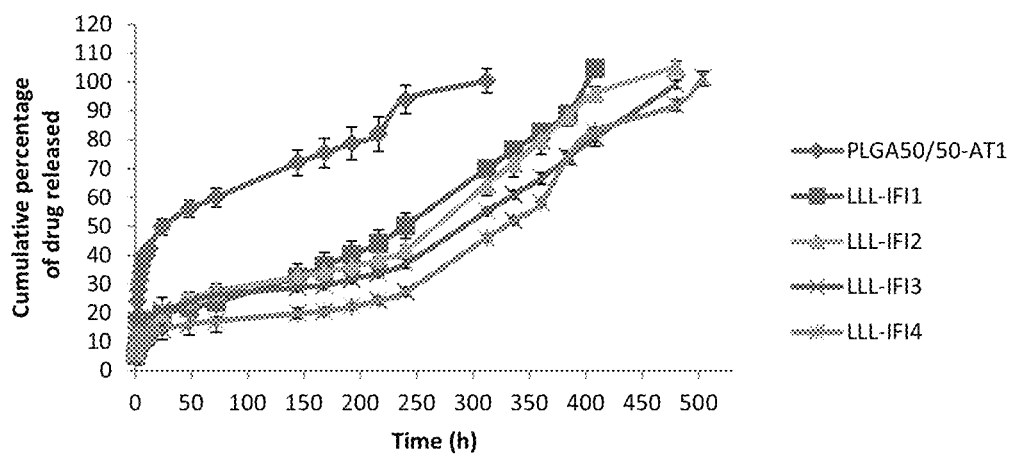
FIG. 4 depicts comparison of release profiles of raloxifene hydrochloride from in-situ forming implant formulations prepared from PLGA lactide to glycolide ratio of 50:50 with acid-terminal group with and without liquid lipids.
Figure 5:
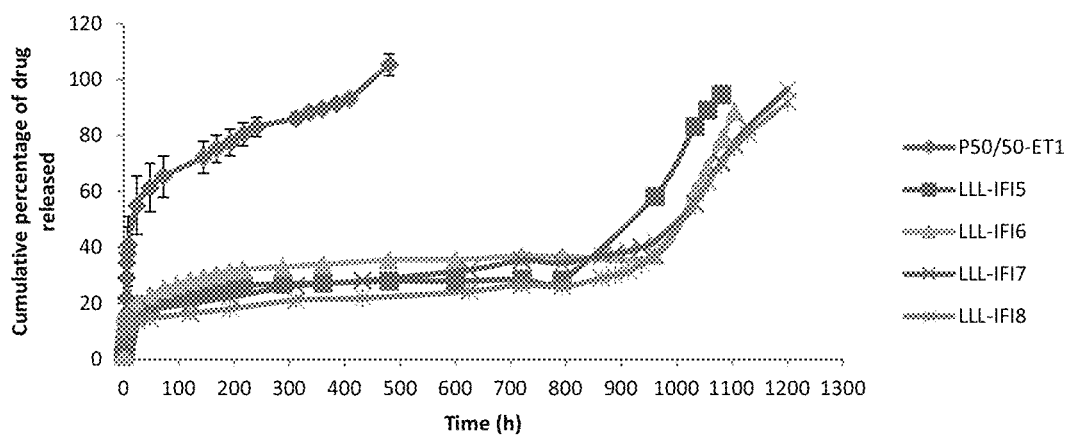
FIG. 5 depicts comparison of release profiles of raloxifene hydrochloride from in-situ forming implant formulations prepared from PLGA lactide to glycolide ratio of 50:50 with ester-terminal group with and without liquid lipids.
Figure 6:
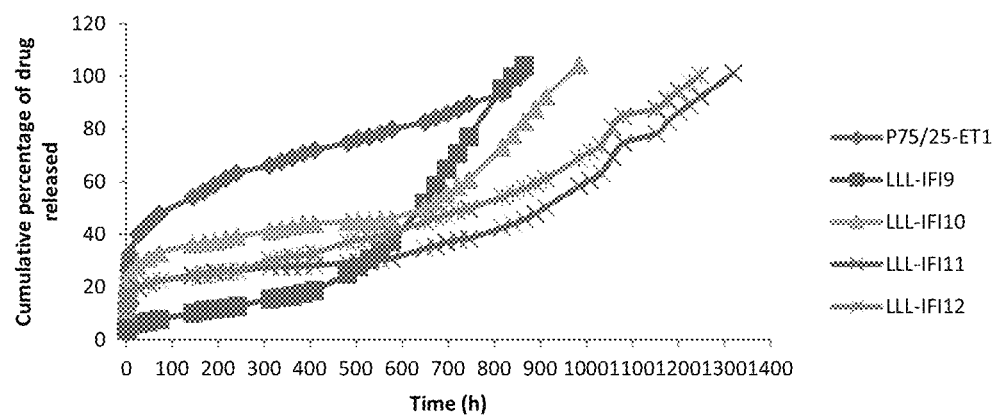
FIG. 6 depicts comparison of release profiles of raloxifene hydrochloride from in-situ forming implant formulations prepared from PLGA lactide to glycolide ratio of 75:25 with ester-terminal group with and without liquid lipids.

The effect of liquid lipids on the in-vitro release of RLX from the PLGA-based in-situ implant formulations Results in Table 3 revealed that PLGA in-situ forming implant formulations (comparative examples) has burst release effect of RLX ranged from 40 to 55% after 24 hrs. This percentage was decreased to 14-28% after the addition of liquid lipids. Moreover, the presence of liquid lipids resulted in extended release for longer time which reached to about 2 months (FIGS. 4-6).

The mean dissolution time (MDT) for each formulation was calculated using KinetDS software (version 3.0, Poland). MDT is the arithmetic mean value of any release profiles. It is used to characterize the drug release rate from the dosage form and the retarding efficacy of the polymer. A higher MDT value indicates a higher drug-retarding ability of the polymer and vice versa. The results of the MDT values for liquid lipids containing formulations were between 2 to 8 folds longer than those lacking the liquid lipids (Table 3).

TABLE 3

Percentage of RLX released after 24 hrs of the in-vitro study

| Polymer | Liquid lipid | Initial burst release (%) | Mean dissolution time (MDT) (hs) |
|---|---|---|---|
| PLGA 50:50 acid terminal (10% w/v) | — | 49.67 ± 2.66 | 82.035 |
| PLGA 50:50 acid terminal (10% w/v) | Labrasol ® | 19.48 ± 5.88 | 212.067 |
| PLGA 50:50 acid terminal (10% w/v) | Labrafac ® | 20.14 ± 1.02 | 222.170 |
| PLGA 50:50 acid terminal (10% w/v) | 1-monolinolein | 20.81 ± 0.92 | 249.293 |
| PLGA 50:50 acid terminal (10% w/v) | 1-monoolein | 14.37 ± 3.60 | 286.227 |
| PLGA 50:50 ester terminal (10% w/v) | — | 55.18 ± 10.45 | 100.802 |
| PLGA 50:50 ester terminal (10% w/v) | Labrasol ® | 17.49 ± 1.89 | 704.427 |
| PLGA 50:50 ester terminal (10% w/v) | Labrafac ® | 20.01 ± 6.47 | 682.656 |
| PLGA 50:50 ester terminal (10% w/v) | 1-monolinolein | 15.43 ± 5.47 | 756.804 |
| PLGA 50:50 ester terminal (10% w/v) | 1-monoolein | 14.15 ± 1.5 | 802.465 |
| PLGA 75:25 ester terminal (10% w/v) | — | 40.07 ± 1.57 | 248.100 |
| PLGA 75:25 ester terminal (10% w/v) | Labrasol ® | 26.23 ± 0.46 | 485.310 |
| PLGA 75:25 ester terminal (10% w/v) | Labrafac ® | 28.36 ± 7.88 | 471.935 |
| PLGA 75:25 ester terminal (10% w/v) | 1-monolinolein | 19.56 ± 0.99 | 728.267 |
| PLGA 75:25 ester terminal (10% w/v) | 1-monoolein | 19.33 ± 0.07 | 639.445 |

In-Vitro Solidification Time for Liquid Lipid Based-PLGA IFI Formulations

A dialysis membrane/solidification time method was used to investigate the in-vitro solidification time for the investigated preparations. Briefly; a 6 cm long dialysis membrane was fixed through a piece of foam in a 100 mL beaker; pre-filled with 80 mL phosphate buffer saline; pH 7.4. The dialysis membrane was secured using a piece of string from its lower side and was totally immersed in the phosphate buffer saline. One mL of each formulation was injected inside the dialysis membrane. The whole beaker was inserted in thermostatically controlled water bath (Unimax, IKA, Germany) at 37° C. to simulate the body temperature. The solidification time was considered as the time required for complete stopping of flow of the liquid formulation inside the dialysis membrane. This was monitored by tilting the beaker every minute.

The results show in-vitro solidification time ranged from 1.5 to 15.0 min.

Injectability Test for Liquid Lipid Based-PLGA IFI Formulations

Fixed volumes of the investigated samples (1 mL) were separately filled into 3 mL syringe attached to 19 gauge needle. The syringe was connected to the air pump through a rubbery tube. Following, air from the air pump was forced onto the solution surface. The pressure of the forced air was kept constant at 70 mmHg using a sphygmometer. The time taken to release the investigated volume of the sample from the syringe was recorded. The values of the flow-rate (mL/min) were calculated.

The results show flow rate values ranged from 0.23 to 2.12 mL/min

Scanning Electron Microscopy for Liquid Lipid Based-PLGA IFI Formulations

The surface morphologies and the cross-sections of PLGA implants were studied by SEM (Model Quanta 250 FEG, Field Emission Gun, FEI company, Netherlands). Prior to investigation, the tested samples were injected into phosphate buffer saline solution (pH=7.4) for implant formation. After that, the implants were removed from the buffer solution after different time intervals (24, 168 and 720 h) from the formation of the implant. The formed implants were then removed and allowed to dry for 2 days in a desiccator. The dried samples were mounted on metal stubs with double sided carbon tape. The samples were then underwent imaging using SEM at an excitation voltage of 20 kv.

FIG. 7 gives detailed information about the surface morphology of $LLL\text{-}IFI_n$ after 24, 168 and 720 h from the formation of the implant. Twenty four hours after injecting $LLL\text{-}IFI_{11}$ into the buffer medium, the formed implant possessed a rough, non-porous surface (FIG. 7A). The absence of the porosity in formulation $LLL\text{-}IFI_{11}$ might be attributed to the presence of 1-monolinolein (liquid lipid) which filled the pores and gives slow solidification time resulting in more time for the formation of the dense implant structure. After 168 h (one week) of the implant formation, small pores began to appear distributed all over the implant (FIG. 7B). After one month of implant formation, the pores increased in size (FIG. 7C) which may be due to the depletion of the oil content by time. This confirms the significant role of the added liquid lipids in controlling the burst effect as well as extending the duration of the drug release and restoring the implant's porous structure.

Gamma Sterilization

The in-situ forming implant formulations were subjected to gamma sterilization using a gamma irradiator (Gamma cell 1000; BEST Theratronics, Ontario, Canada). During the gamma sterilization process the formulations were packed inside polyurethane containers pre-filled with dry ice to avoid the elevation in temperature during the sterilization process which could result in particles melting or aggregation. After sterilization, the formulations were re-evaluated for their in-vitro release, in-vitro solidification time and injectability test. To confirm that there was no effect on the release pattern of the drug after sterilization, the similarity factor (f2) between the sterilized and the non-sterilized formulations was calculated to identify the degree of similarity between their in-vitro release profiles applying the following equation $$f_2 = 50 \cdot \log\left[\left\{1 + \left(\frac{1}{n}\right)\sum_{t=1}^{n}(R_t - T_t)^2\right\}^{-0.5} \cdot 100\right]$$

Where, n is denoted or the sampling number, and T are the percentage drug released from the similar sample before and after the sterilization process at every time point t. After the gamma sterilization process, it was proven that no significant difference (P>0.05) in solidification time and injectability (flow rate) was detected between the investigated formulations before and after the sterilization process. After comparing the in-vitro release profiles of the investigated formulations before and after the gamma sterilization, it was clear that both release profiles were identical. This was confirmed after calculating the similarity factor (f). The obtained similarity factor (f) was above 50. Similarity factor (f) with values ranging between 51 and 100 indicate similar release profiles. Hence, it could be confirmed that the applied gamma sterilization process didn't affect the physicochemical characters of the tested formulations.

In-Vivo Animal Studies

Twenty-four adult male Sprague-Dawley rats weighing 250-300 g were included in the study. The animals were quarantined separately in special cages, 4 rats in each cage, with free access to food (standard diet) and water. The quarantine room was air-conditioned at 25f0.5° C. and illuminated with artificial fluorescent light on two cycles of day and night, 12 h each.

Prior to dosing of the selected formulations, the animals were generally anesthetized using intramuscular injection of a mixture of ketamine (50 mg/mL) and xylazine (20 mg/mL) mixed at a ratio of 2:1 into the gluteal muscles given at a dose of 1 mL/kg body weight. The anesthetized animals were subjected to a surgical operation in which a uni-cortical defect with size of 2 mm in diameter was formed in the tibia of both the left and right limbs by standardized surgical procedures. Simply, a 1 cm skin incision was made on the medial side of the tibia using a sterilized 2 mm globular drill (Strong, micro-drill, China), after that the muscles were dissected and the periosteum was stripped exposing the tibial bone. The formed defects were then irrigated with sterile saline, in triplicates. The incision was sutured using absorbable sutures, the animals were given intramuscular injection of ceftriaxone HCl (20 mg/kg) once daily for 5 successive days and the wounds were daily cleaned with povidone iodine (10% w/v).

The twenty-four rats (with formed bone injuries) were divided into two groups of equal size (A and B). After one week from the surgery, group (A) received the selected PLGA in-situ forming implant (without liquid lipid). Group (B) received the corresponding selected liquid lipid-based PLGA in-situ forming mixed implant (with liquid lipid). All the investigated formulations were injected through skin using syringe in the right leg while the left leg in each rat was kept as control.

Histological Assay

At the end of each time interval, four rats were generally anesthetized intramuscularly using 1 mg/kg of a mixture of ketamine (50 mg/mL) and xylazine (20 mg/mL) at a volume ratio of 2:1 into the gluteal muscle and sacrificed using overdose of thiopental. Following, the tibias were isolated, and all soft tissues were removed and preserved in 10% buffered para-formaldehyde solution (10%).

Autopsy samples were taken from the tibia of the rats' bone from different groups and fixed in 10% formalin saline solution for 24 h then decalcified in 5% formic acid for 6 weeks. After decalcification, washing was done using tap water followed by serial dilutions of alcohol (methanol, ethanol and absolute ethanol) for dehydration. Specimens were cleared in xylene and embedded in paraffin at 56° C. in hot air oven for 24 h. Paraffin bees wax tissue blocks were prepared for sectioning at 4 microns thickness by sledge microtome. The obtained tissue sections were collected on glass slides, de-paraffinized, stained by hematoxylin and eosin stain for examination through the light electric microscope (CX21Olympusmicroscope, Tokyo, Japan). FIGS. 8A-8C represent the photomicrographs of the stained sections obtained from the rats' tibia with induced punctures after time intervals of 3, 6 and 12 weeks from injecting the investigated formulations in the bone defect. After 3 weeks of the study the untreated rats' tibias punctured area showed osteoporosis associated with fibrous osteodystrophy of the bone trabeculae and chondro-mucinous degeneration with the appearance of proliferated osteoblasts in the surrounding area (FIG. 8A). Unlike the untreated punctured area after 3 weeks of the study, the punctured area treated with P75/25-$ET_1$ was filled with proliferated osteoblasts which were unevenly distributed and fibrous tissues appeared in the injured tissue indicating callus tissues formation. Callus tissues are required for bone matrix formation which provide the ductility and the ability to absorb energy (FIG. 8B). On the other hand, fibroblastic cells proliferation in the damaged area as well as cartilaginous resorption appeared after 3 weeks from injecting LLL-$IFI_{11}$ in the rat-tibia punctured area which gives an indication that the callus begin to appear (FIG. 8C). That reparative phase began after three weeks of the treatment indicating accelerated bone recovery compared to that for the control group.

In the control group the callus tissues began to appear in the untreated punctured area after six weeks which was filled with collagen fibers and fibrous connective tissues (FIG. 8B). On the other hand, after 6 weeks from injecting the punctured area with P75/25-$ET_1$, nearly complete filling of the punctured area with uneven distributed osteoblasts and fibroblasts occurred with the replacement of some fibrous tissues with calcified ones. An early stage of the reparative phase appeared after 6 weeks from injecting LLL-$IFI_{11}$ in the punctured area which was indicated by the appearance of collagen and fibroblasts in the punctured area and absence of osteoblasts and calcified tissues.

The untreated punctured area showed focal area of haemolysederythroid cells surrounded by regenerated osteoblasts after 12 weeks of beginning of the study. The histopathological data of the punctured rat-tibia treated with P75/25-$ET_1$ showed complete healing of the punctured area with newly formed bone surface with small osteonal canals, organized fibrous tissues and large number of unhomogenously distributed osteoblasts. However, there was complete replacement of the fibrous tissues with homogenously distributed high density osteoblasts on the compact newly formed bone indicating complete healing of the punctured area upon injecting the punctured area with LLL-$IFI_{11}$. This homogenous distribution of osteoblasts will induce homogenous matrix mineralization indicate bone maturation.

This pronounced progress in the healing of the punctured area after 12 weeks from injecting LLL-IFI$_{11}$ may be due to the prolonged release of the drug from this formulation as well as the formation of porous structure after about one month from injecting LLL-IFI$_{11}$ in the inducted puncture. This porous structure was formed due to the diffusion of the liquid lipid outside the PLGA matrix by time as manifested by the SEM. This porous structure made the implant to act as supporting scaffold which facilitated the transport of oxygen and nutrients and control cell proliferation. These results revealed that injecting the liquid lipid based PLGA formula; in the bone injury resulted in formation of higher regularly oriented structured bone after 12 weeks compared to the bone formed after injecting the regular PLGA formula; without liquid lipid.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. An In-situ forming implant formulation comprising: poly (lactide-co-glycolide) (PLGA) copolymer in concentration range from 5% to 20% w/v, a selective estrogen receptor modulator, 1-monolinolein in concentration range from 5% to 10% w/v, and an organic solvent.

2. The In-situ forming implant formulation according to claim 1, wherein the concentration of PLGA copolymer is in concentration of 10% w/v.

3. The In-situ forming implant formulation according to claim 1, wherein the PLGA copolymer is ester terminated comprising lactide to glycolide ratio of 50:50.

4. The In-situ forming implant formulation according to claim 1, wherein the PLGA copolymer is ester terminated comprising lactide to glycolide ratio of 75:25.

5. The In-situ forming implant formulation according to claim 1, wherein the selective estrogen receptor modulator is selected from tamoxifene, tormifene, raloxifene and bazedoxifene, and pharmaceutically acceptable salts thereof.

6. The In-situ forming implant formulation according to claim 5, wherein the selective estrogen receptor modulator is raloxifene hydrochloride.

7. The In-situ forming implant formulation according to claim 1, wherein the concentration of 1-monolinolein is 10% w/v.

8. The In-situ forming implant formulation according to claim 1, wherein the organic solvent is selected from N-methyl-2 pyrrolidone, tetrahydrofuran, methyl acetate, ethyl acetate, dimethyl formamide, dimethyl sulfoxide, dimethylsulfone, triacitin, and propylene glycol.

9. The In-situ forming implant formulation according to claim 1, wherein the organic solvent is dimethyl sulfoxide.

10. The In-situ forming implant formulation according to claim 1 comprising 10% w/v 75:25 PLGA ester terminated, 1% w/v raloxifene hydrochloride, 10% w/v 1-monolinolein, and dimethyl sulfoxide.

* * * * *